US010716683B2

(12) United States Patent
Termanini et al.

(10) Patent No.: US 10,716,683 B2
(45) Date of Patent: Jul. 21, 2020

(54) BALL AND CUP IMPACTORS FOR IMPLANTING A HIP PROSTHESIS

(71) Applicant: HIP INNOVATION TECHNOLOGY, LLC, Boca Raton, FL (US)

(72) Inventors: Zafer Termanini, Port Saint Lucie, FL (US); Brian Vanhiel, Smyrna, GA (US); Kirk Charles, Austell, GA (US)

(73) Assignee: HIP INNOVATION TECHNOLOGY LLC, Boca Raton, FL (US)

( * ) Notice: Subject to any disclaimer, the term of this patent is extended or adjusted under 35 U.S.C. 154(b) by 0 days.

(21) Appl. No.: 16/156,671

(22) Filed: Oct. 10, 2018

(65) Prior Publication Data

US 2019/0038431 A1 Feb. 7, 2019

Related U.S. Application Data

(62) Division of application No. 15/742,252, filed as application No. PCT/US2016/042441 on Jul. 15, 2016.

(Continued)

(51) Int. Cl.
*A61F 2/46* (2006.01)
*A61F 2/34* (2006.01)
(Continued)

(52) U.S. Cl.
CPC .......... *A61F 2/4609* (2013.01); *A61F 2/4637* (2013.01); *A61F 2/34* (2013.01);
(Continued)

(58) Field of Classification Search
CPC .... A61F 2/4609; A61F 2/4603; A61F 2/4637; A61B 17/92
See application file for complete search history.

(56) References Cited

U.S. PATENT DOCUMENTS

| 5,284,483 A | 2/1994 | Bayliss et al. |
| 5,549,696 A | 8/1996 | Willi |

(Continued)

FOREIGN PATENT DOCUMENTS

| FR | 1456048 A1 | 5/1966 |
| FR | 3016282 A1 | 7/2015 |

(Continued)

OTHER PUBLICATIONS

International Search Report for related application PCT/US2016/042441 dated Oct. 13, 2016, previously submitted in the parent application.

(Continued)

*Primary Examiner* — Amy R Sipp
(74) *Attorney, Agent, or Firm* — Norris McLaughlin, PA

(57) ABSTRACT

New surgical instruments and methods used to implant elements of a reverse hip prosthesis in a patient are described. The instruments are impactors which are struck with a hammer at their proximal ends after the instrument has been used to position the implant element in the patient. An acetabular cup impactor has inclination and anteversion rods which are used to position the acetabular cup optimally in the acetabulum. An acetabular ball impactor affixes the acetabular ball in the acetabular cup by means of a Morse taper. And a femoral cup impactor affixes the femoral cup in the femoral stem by means of a Morse taper.

8 Claims, 6 Drawing Sheets

Related U.S. Application Data

(60) Provisional application No. 62/197,215, filed on Jul. 27, 2015.

(51) Int. Cl.
*A61F 2/30* (2006.01)
*A61F 2/36* (2006.01)

(52) U.S. Cl.
CPC ............ *A61F 2002/30332* (2013.01); *A61F 2002/3483* (2013.01); *A61F 2002/3615* (2013.01); *A61F 2002/4627* (2013.01)

(56) References Cited

U.S. PATENT DOCUMENTS

| | | |
|---|---|---|
| 5,674,225 A | 10/1997 | Muller |
| 6,063,124 A | 5/2000 | Amstutz |
| 2003/0229357 A1* | 12/2003 | Dye .................... A61F 2/4637 606/99 |
| 2005/0085823 A1 | 4/2005 | Murphy |
| 2005/0228395 A1 | 10/2005 | Auxepaules et al. |
| 2007/0219562 A1 | 9/2007 | Slone et al. |
| 2007/0293869 A1 | 12/2007 | Conte et al. |
| 2011/0218637 A1* | 9/2011 | Termanini ................ A61F 2/34 623/22.15 |
| 2012/0059383 A1* | 3/2012 | Murphy ................ A61F 2/4612 606/99 |
| 2012/0184965 A1 | 7/2012 | Burgi |
| 2013/0331849 A1 | 12/2013 | Splieth et al. |

FOREIGN PATENT DOCUMENTS

| | | |
|---|---|---|
| WO | 2014147529 A1 | 9/2014 |
| WO | 20150044680 A1 | 4/2015 |

OTHER PUBLICATIONS

Written Opinion of the International Searching Authority for related application PCT/US2016/042441 dated Oct. 13, 2016, previously submitted in the parent application.
EP Search Report for corresponding application EP 16831036.5 dated Apr. 30, 2020.

* cited by examiner

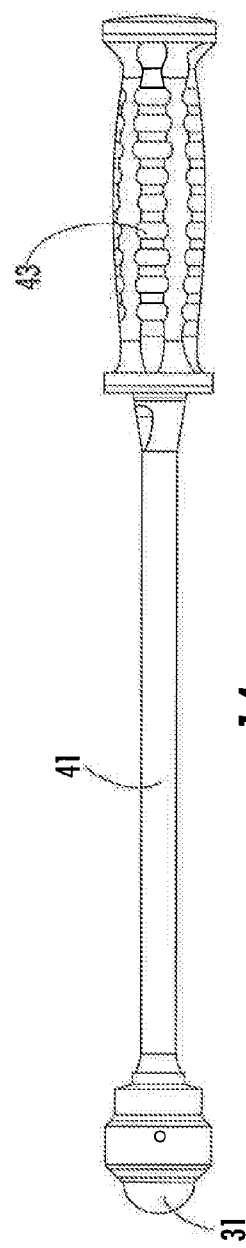
FIG. 14
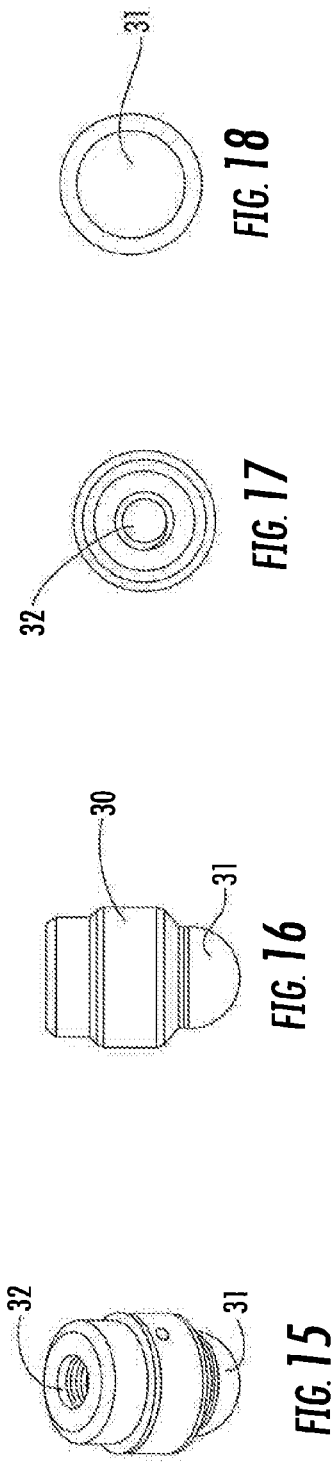
FIG. 15
FIG. 16
FIG. 17
FIG. 18

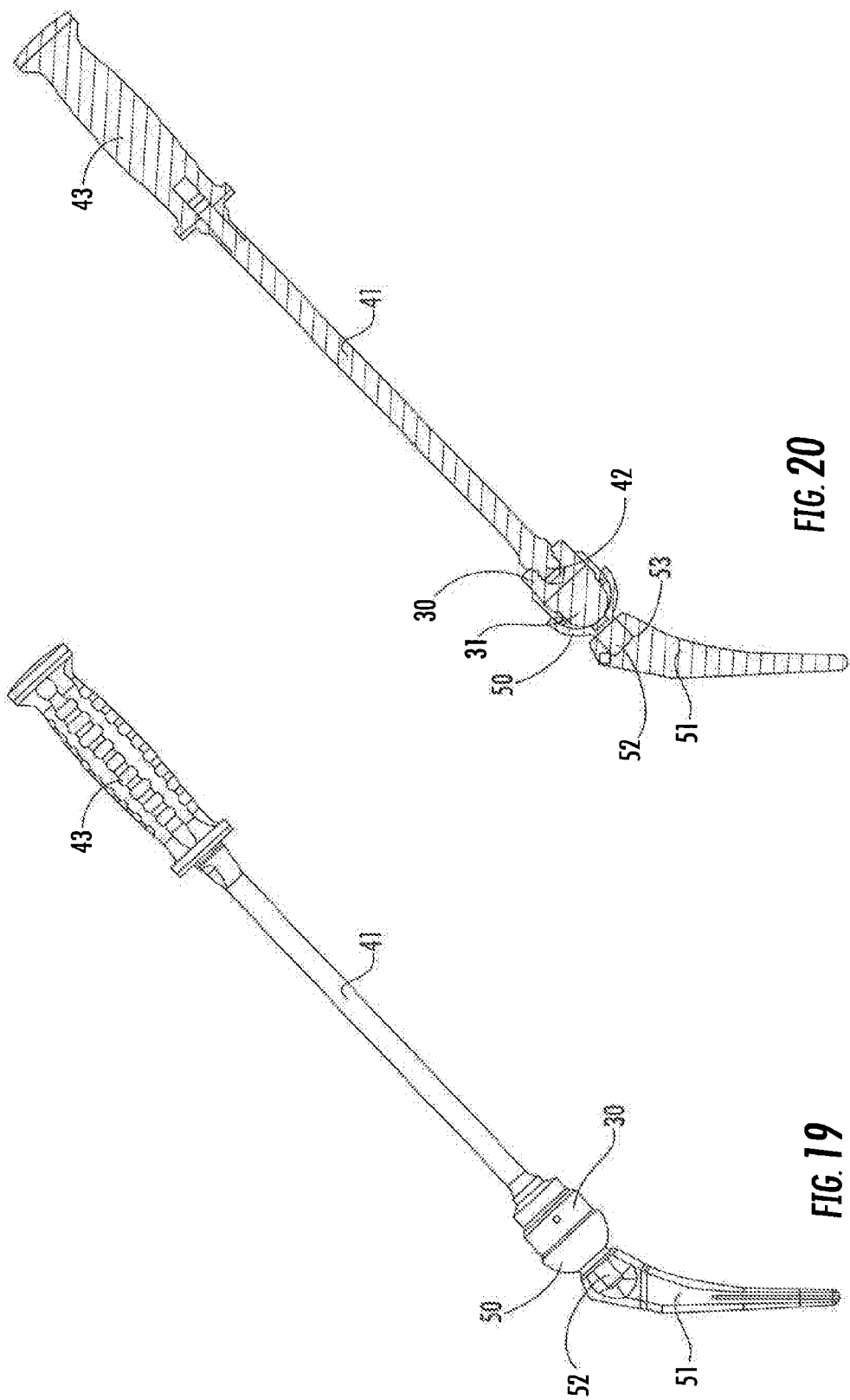

BALL AND CUP IMPACTORS FOR IMPLANTING A HIP PROSTHESIS

This is a Divisional patent application of U.S. Ser. No. 15/742,252, which in turn is an application filed under 35 USC 371 based on PCT/US2016/042441 filed 15, Jul. 2016, which in turn claims priority to U.S. Ser. No. 62/197,215 filed 27, Jul. 2015. The present application claims the full priority benefit of these prior applications and incorporates by reference the full disclosures of these prior applications as if set forth herein.

BACKGROUND OF THE INVENTION

Field of the Invention

The present invention relates to surgical instruments used in connection with implanting a reverse hip prosthesis in a patient. More particularly, the invention has to do with impactors for implanting an acetabular cup, an acetabular ball and a femoral cup.

The Related Art

A reverse hip prosthesis is described in U.S. Pat. Nos. 8,313,531 B2 and 8,540,779 B2. The prosthesis and a revision surgery method also are described in U.S. Pat. No. 8,992,627 B2. The disclosures of these three patents are incorporated herein in their entireties by reference.

SUMMARY OF THE INVENTION

As described in the patents referenced above, the acetabular cup is affixed in the acetabulum by impacting it therein and then, if needed, affixing it further using screws. The acetabular ball is affixed by means of a Morse taper to a stem extending from the bottom of the concave surface of the acetabular cup and the femoral cup is affixed to the femoral implant (or femoral stem) by means of a Morse Taper. The surgical instruments of the invention, sometimes referred to herein as surgical tools, enable a surgeon to impact each of these components of the prosthesis with optimal placement of the acetabular cup and secure affixation of the acetabular ball and the femoral cup.

BRIEF DESCRIPTION OF THE DRAWINGS

FIG. 14 is an elevation view of a femoral cup impactor assembly.

FIG. 15 is a perspective view of a femoral cup impactor.

FIG. 16 is a side elevation view of FIG. 15.

FIG. 17 is a top elevation view of FIG. 16.

FIG. 18 is a bottom elevation view of FIG. 16.

FIG. 19 is an elevation view of a femoral cup impactor assembly and a femoral cup positioned in a femoral implant, the femoral implant being illustrated in section.

FIG. 20 is a section view of FIG. 19.

DESCRIPTION OF THE PREFERRED EMBODIMENTS

The impactors of the present invention are used to implant in a patient three elements of a reverse hip prosthesis. The elements are the acetabular cup, the acetabular ball and the femoral cup.

Figure 1:
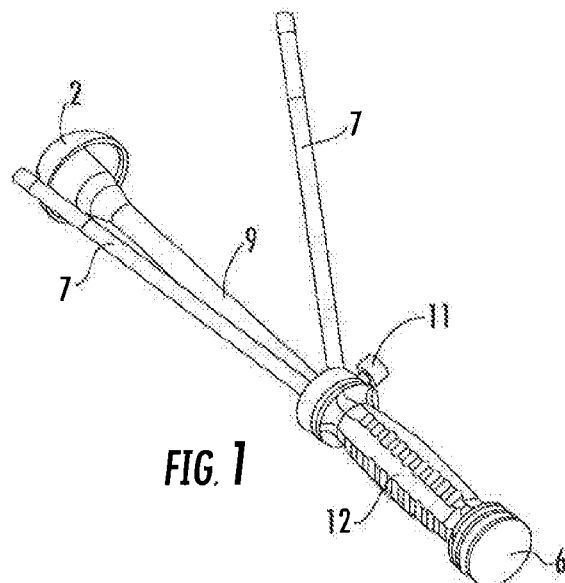
FIG. 1 is a perspective view of the acetabular cup impactor assembly of the invention.
Figure 2:
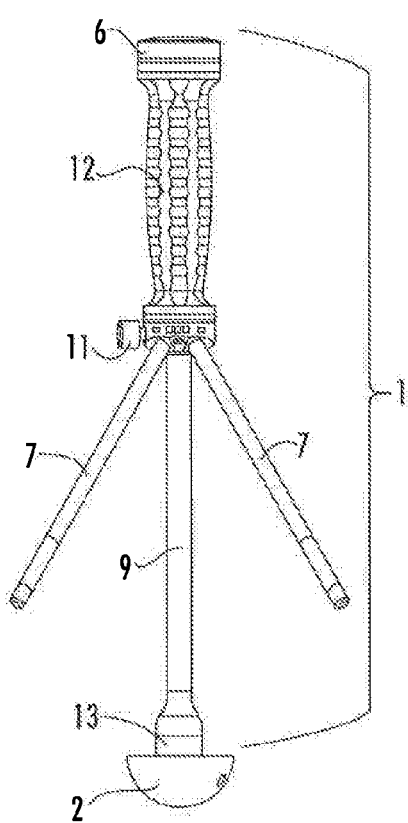
FIG. 2 is an elevation view of the acetabular cup impactor assembly.
Figure 3:
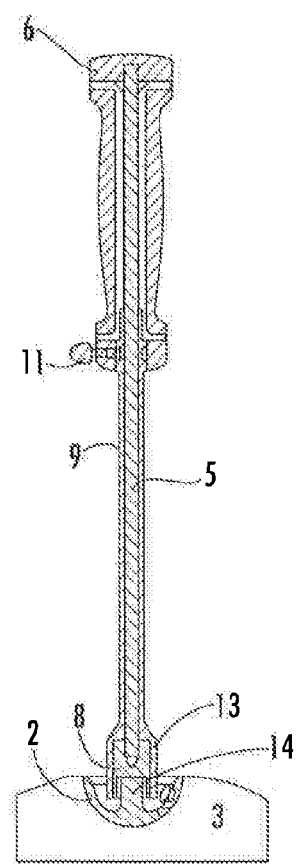
FIG. 3 is a section view of FIG. 2 illustrating a partial acetabular bone element.

Following preparation of the acetabulum to receive the acetabular cup, the acetabular cup is positioned in the acetabulum and impacted therein using the acetabular cup impactor assembly 1 illustrated in FIGS. 1-4. Elements of acetabular cup impactor assembly 1 are illustrated in FIGS. 5-8. FIGS. 1-3 illustrate acetabular cup 2 in relation to the assembly 1 and FIG. 3 includes a portion of the acetabulum 3.

Figure 4:
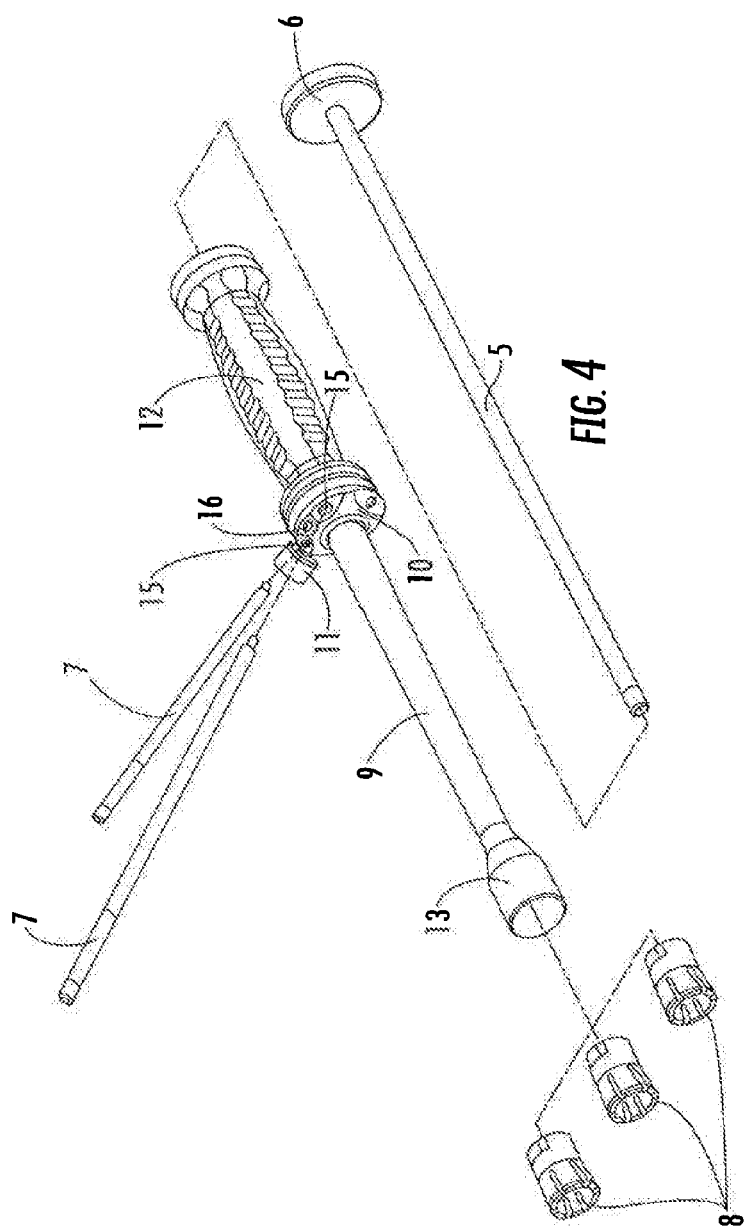
FIG. 4 is an exploded view of the acetabular cup impactor assembly.
Figure 5:
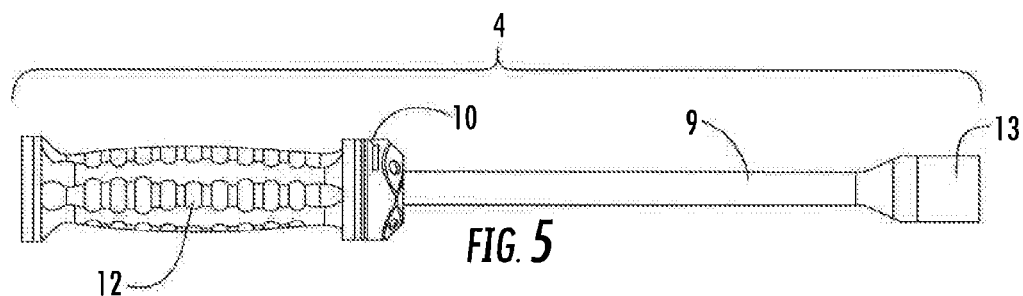
FIG. 5 is an elevation view of an acetabular cup handle for the acetabular cup impactor assembly.
Figure 6:
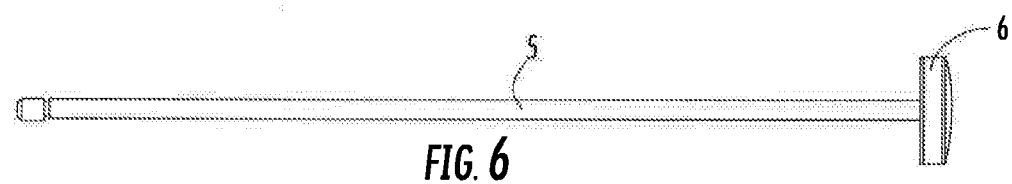
FIG. 6 is an elevation view of an inner shaft for the acetabular cup impactor assembly.
Figure 7:
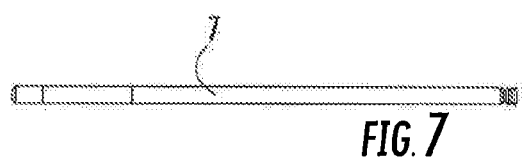
FIG. 7 is an elevation view of an inclination-anteversion guide rod for the acetabular cup impactor assembly.

The acetabular cup impactor assembly 1 is comprised of acetabular cup handle 4, having a channel extending annularly along the length thereof, the channel being open at the proximal and distal ends of the handle 4, inner shaft 5 having a knob 6 at the proximal end thereof, inclination-anteversion guide rods 7 and collet 8. Guide rods 7 are threaded at their distal ends. The acetabular cup handle 4 has a handle shaft 9 and an inclination-anteversion guide collar 10 rotatably mounted on handle shaft 9. Inclination-anteversion guide collar 10, sometimes referred to herein as rotatable guide 10, has threaded holes (See FIG. 4.) designated as anteversion holes 15 and inclination hole 16. A rod 7 is threaded into hole 16 and one of holes 15, depending on whether the right or left hip is being replaced. Thumb screw 11 is tightened to prevent rotation of guide collar 10 when a rod 7 is optimally positioned during surgery. Handle element 12 is affixed proximally on shaft 9 and sleeve 13 is affixed to the distal end of shaft 9. The sleeve 13 has a tapered annular inner portion, the taper narrowing in the proximal direction, the tapered annular inner portion of the sleeve 13 being sized to cause a distal end of the collet 8 to contract when the collet 8 moves into the sleeve 13 in a proximal direction. FIG. 4 illustrates three collets 8, each being of a different size for different sizes of acetabular cups 2. Acetabular cup 2 has a stem 14 projecting from the bottom of the concave surface thereof. The size of the collet 8 refers to an annular inner portion thereof which is sized to releasably grip a proximal portion of the stem 14. The collet 8 grips the stem 14 when the collet 8 is contracted and releases the stem 14 when the collet 8 is open, i.e., not contracted.

In the surgical method of the invention, the acetabulum 3 is prepared to receive an appropriately sized acetabular cup 2 and a collet 8 sized for the cup is selected. Inner shaft 5 is inserted into the distal end of acetabular cup handle 4 and the collet 8 is then attached to the distal end of inner shaft 5. The collet 8 is then pushed over the stem 14 of acetabular cup 2 and the collet 8 is pulled into sleeve 13 so that the collet 8 firmly grips the stem 14. This causes shaft 5 to move proximally leaving a space between knob 6 and the proximal end of handle element 12. An inclination-anteversion guide rod 7 is threaded into hole 16 of inclination-anteversion guide collar 10, another inclination-anteversion guide rod 7 is threaded into a hole 15 (see FIG. 4), and the acetabular cup 2 is placed in acetabulum 3. Then the screw holes in cup 2 are aligned properly in the acetabulum for eventual fixation of the cup to the acetabulum using screws. The inclination-anteversion guide collar 10 is then rotated until the rods 7 are properly positioned and thumb screw 11 then is tightened. It should be noted that the guide rods are set at a 45 degree angle relative to the shaft 9 and at a 20 degree angle relative to one another. The surgeon sets the inclination using the rod threaded into hole 16 by keeping the rod parallel to the floor and pointing it toward the shoulder of the patient. If a left hip is being replaced it is pointed at the left shoulder and if a right hip is being replaced it is pointed at the right shoulder. When the inclination is set, the surgeon then sets the anteversion using the rod 7 threaded into a hole 15. Either hole 15 is used, depending on whether the right hip or left hip is being replaced as will be apparent to those having ordinary skill in the art based on the disclosures herein. The anteversion rod creates 20 degrees of anteversion with the inclination rod by orienting the anteversion rod toward the same shoulder. The rods are used in this manner with a posterior surgical approach and this properly sets the orientation of the cup 2 at a compound angle of 45 degrees of inclination and 20 degrees of anteversion. The assembly is maintained in position by holding handle element 12 as the proximal end of knob 6 is struck with a hammer thereby impacting the acetabular cup in the acetabulum. Assembly 1 is then removed from the operating site.

Figure 9:
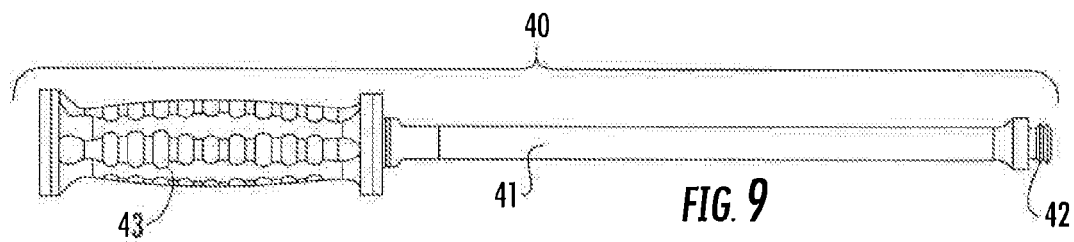
FIG. 9 is an elevation view of a universal handle for the acetabular ball impactor assembly and the femoral cup impactor assembly.
Figure 8:
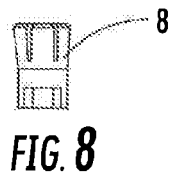
FIG. 8 is an elevation view of a collet for the acetabular cup impactor assembly.
Figure 13:
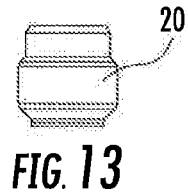
FIG. 13 is an elevation view of an acetabular ball impactor.
Figure 13A:
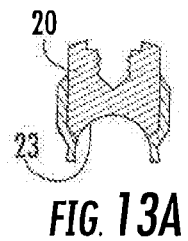
FIG. 13A is a section view of the acetabular ball impactor of FIG. 13.
Figure 10:
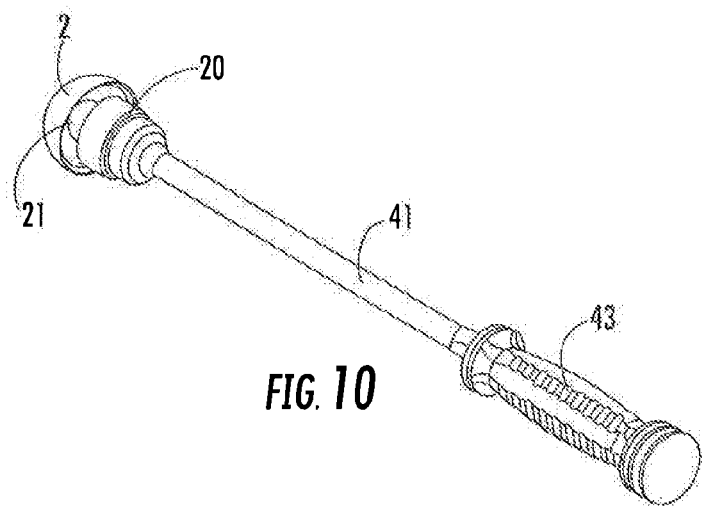
FIG. 10 is a perspective view of an acetabular ball impactor assembly, acetabular ball and acetabular cup.
Figure 11:
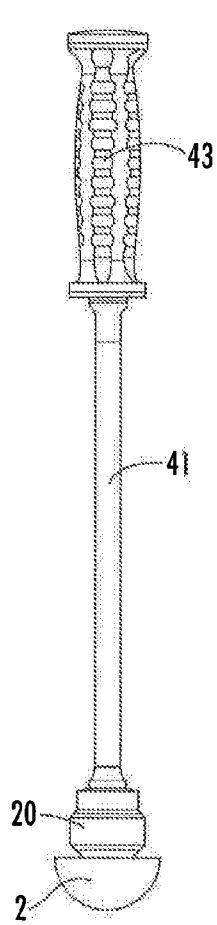
FIG. 11 is an elevation view of FIG. 10.
Figure 12:
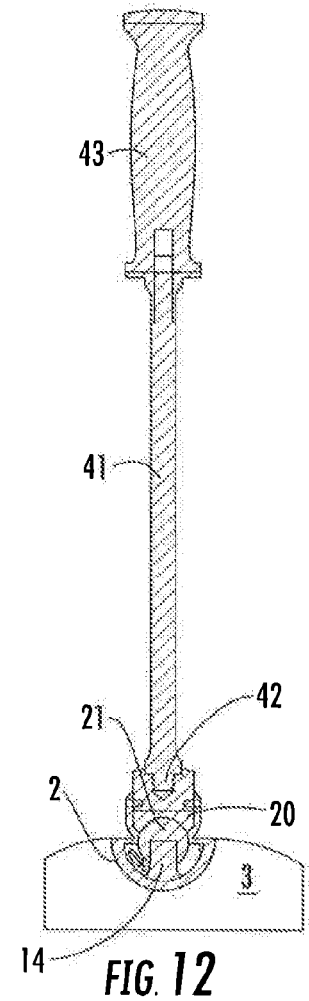
FIG. 12 is a section view of FIG. 11 with an added acetabular bone element.

An acetabular ball impactor assembly is illustrated in FIGS. 10-12 and the acetabular ball impactor 20 is illustrated in elevation in FIG. 13. The acetabular ball impactor assembly 13 is comprised of acetabular ball impactor 20 and universal handle 40. (See also FIG. 9). The universal handle 40 is comprised of shaft 41 having a threaded portion 42 at its distal end and a handle element 43 at its proximal end. The acetabular ball impactor 20 has a proximal end and a distal end. As illustrated in FIG. 13A, the proximal end of acetabular ball impactor 20 has threads 22 and the distal end has a concave surface portion 23. The concave surface portion being in the shape of a section of a sphere. The threaded portion 42 is threaded into the threads 22 of the acetabular ball impactor 20.

Acetabular ball impactor 20 is made in sizes compatible with differently sized acetabular balls 21. When a ball 21 is selected, it is placed over stem 14 of acetabular cup 2. The appropriately sized acetabular ball impactor 20 is threaded onto the universal handle 40 and the concave surface of acetabular ball impactor 20 is placed over the ball, allowing the ball to be received therein. Appropriate sizing in this context means the concave surface portion of the acetabular ball impactor is sized to receive the acetabular ball. Thus the concave surface has the shape of a section of a sphere and a size the same as or approximately the same as the spherical size of the acetabular ball to be received therein. With the universal handle 40 held in a position wherein the central axis of the stem 14 and the central axis of the shaft 41 are in the same or approximately the same line (as illustrated in FIGS. 11 and 12) the proximal end of handle element 43 is struck with a hammer to cause the acetabular ball 21 to be firmly affixed to stem 14 by means of the Morse taper.

A femoral cup impactor 30 is illustrated in FIGS. 15-18. It is comprised of a convex surface portion, referred to herein as impactor tip 31, at its distal end and a threaded portion 32 at its proximal end. The convex surface portion is in the shape of a sphere. Threaded portion 32 is used to affix the impactor to universal handle 40. When the femoral cup impactor 30 is affixed to universal handle 40, the combination of elements is referred to herein as a femoral cup impactor assembly.

FIGS. 19 and 20 further illustrate the femoral cup impactor, a femoral cup 50 and a femoral implant 51. The femoral cup 50 has a stem 52 which is sized to fit in a Morse taper relationship in recess 53 of femoral stem 51.

Femoral cup impactor 30 is made in sizes compatible with differently sized femoral cups 50. The femoral cup 50 has a concave surface portion in the shape of a section of a sphere sized to articulate on acetabular ball 21. When a femoral cup 50 is selected, the stem 52 is placed in recess 53. The appropriately sized acetabular cup impactor is threaded onto the universal handle 40 and the convex impactor tip 31 is placed into the concave portion of femoral cup 50. Appropriate sizing in this context means the convex surface of the femoral cup impactor is sized to be received in the concave surface portion of the femoral cup. Thus the convex surface has the shape of a section of a sphere and a size the same as or approximately the same as the concave surface portion of the femoral cup. Thus the convex surface has the shape of a section of a sphere and a size the same as or approximately the same as the concave surface portion of the femoral cup. With the universal handle 40 held in a position wherein the central axis of the stem 52 and the central axis of the shaft 41 are in the same or approximately the same line (as illustrated in FIGS. 19 and 20) the proximal end of handle element 43 is struck with a hammer to cause the femoral cup 50 to be firmly affixed to femoral implant 51 by means of the Morse taper.

The surgical instruments of the invention may comprise a portion of surgical kits. The kits may contain one or more than one of the surgical instruments of the invention along with other surgical instruments and/or implants.

The invention claimed is:

1. An acetabular ball impactor assembly having a handle and and an acetabular ball impactor, the assembly configured to affix an acetabular ball onto a stem of an implanted acetabular cup which has a concave inner surface with the stem extending from the concave inner surface via impaction of the acetabular ball impactor causing the acetabular ball to be affixed to a part of the stem, the acetabular cup being affixed to an acetabulum of a patient, wherein:

the handle comprises a solid shaft having a proximal end, a central axis, and a distal end, a threaded portion at the distal end and a handle element at the proximal end, and the acetabular ball impactor comprises a body with a proximal end and a distal end, threads disposed at the proximal end of the body, the threads sized to receive the threaded portion at the distal end of the shaft, and a circular concave surface extending inwardly from the distal end and into the body and an uninterrupted circumferential part defining a circumferential opening having a circular margin and a diameter approximately equal to or a diameter larger than a diameter of the circular concave surface, the uninterrupted circumferential part and the concave surface being sized to receive the acetabular ball, and further wherein;

a length of the body between a point of the circular concave surface most proximate to the proximal end and the circular margin of the uninterrupted circumferential part is such that an entirety of the circular margin is spaced from the concave inner surface of the implanted acetabular cup when the acetabular ball is affixed to the stem, and the body has a width which at a maximum dimension is smaller than a maximum width of the acetabular cup.

2. A kit containing the acetabular ball impactor assembly of claim 1, and one or more further other surgical instruments and/or implants.

3. The kit of claim 2, which further comprises a surgical instrument configured to impact an acetabular cup into an acetabulum of a patient wherein the acetabular cup has a central stem having a Morse taper extending from a bottom of a concave inner surface thereof, the surgical instrument comprising:

a handle having a proximal end and distal end and a central axis, a sleeve disposed on the distal end concentric with the handle of the surgical instrument and an annular channel extending therethrough, the annular channel being open at the proximal and the distal ends of the handle of the surgical instrument, a shaft having a proximal end and a distal end and a knob affixed to the proximal end, the shaft of the surgical instrument being slidably disposed within the annular channel, a collet removably affixed to the distal end of the shaft of the surgical instrument and proximate the sleeve, wherein the sleeve has a tapered annular inner portion, the tapered annular inner portion narrowing in a proximal direction, the tapered annular inner portion of the sleeve being sized to cause a distal end of the collet to contract and grip the central stem of the acetabular cup and thereby gripping the acetabular cup only by the central stem when the collet moves into the sleeve in the proximal direction, a rotatable guide collar mounted externally on the handle of the surgical instrument and rotatable about the central axis of the handle of the surgical instrument configured to have affixed to the rotatable guide collar a plurality of guide rods wherein each of the guide rods has a proximal end removably affixable to the rotatable guide collar and extending outwardly therefrom at an angle relative to the central axis, wherein at least two of the guide rods, when affixed to the rotatable guide collar are each positioned at a 45 degree angle relative to the shaft of the surgical instrument, and are positioned at a 20 degree angle relative to each other, and the direction of the at least two affixed guide rods are oriented to extend in a distal direction from the rotatable guide collar and a thumb screw having a part extending into the rotatable guide collar wherein rotation of the thumb screw prevents movement of the rotatable guide collar and of any of the guide rods affixed to the rotatable guide collar relative to the handle of the surgical instrument.

4. The kit of claim 3, wherein the collet has a collet inner portion sized to releasably grip a proximal portion of the central stem, gripping the stem when the collet is contracted and releasing the central stem when the collet is not contracted.

5. The kit of claim 3, which comprises a plurality of collets.

6. The kit of claim 5, wherein at least two of the plurality of collets have different sizes.

7. A method of using the acetabular ball impactor assembly of claim 1, the method comprising:

placing an acetabular ball onto a stem of an acetabular cup, positioning a concave surface of the acetabular ball impactor on the acetabular ball, holding the handle in a position wherein a central axis of the stem and the central axis of the shaft are coincident or approximately coincident and then, striking a proximal end of the handle element with a hammer to thereby affix the acetabular ball to a part of the stem extending from the concave inner surface but without contacting any part of the circular margin with the concave inner surface of the implanted acetabular cup.

8. The acetabular ball impactor assembly of claim 1, wherein the concave surface sized to receive the acetabular ball is in the shape of a section of a sphere.

* * * * *